(12) United States Patent
Juels

(10) Patent No.: US 8,886,316 B1
(45) Date of Patent: Nov. 11, 2014

(54) AUTHENTICATION OF EXTERNAL DEVICES TO IMPLANTABLE MEDICAL DEVICES USING BIOMETRIC MEASUREMENTS

(71) Applicant: EMC Corporation, Hopkinton, MA (US)

(72) Inventor: Ari Juels, Brookline, MA (US)

(73) Assignee: EMC Corporation, Hopkinton, MA (US)

( * ) Notice: Subject to any disclaimer, the term of this patent is extended or adjusted under 35 U.S.C. 154(b) by 0 days.

(21) Appl. No.: 13/718,171

(22) Filed: Dec. 18, 2012

(51) Int. Cl.
A61N 1/08 (2006.01)
A61N 1/372 (2006.01)
A61N 1/39 (2006.01)

(52) U.S. Cl.
CPC .......... A61N 1/37252 (2013.01); A61N 1/3937 (2013.01)
USPC .................... 607/31; 607/30; 607/32; 607/59; 607/60

(58) Field of Classification Search
CPC ........................ A61N 1/37211; A61N 1/37252
USPC .......................................... 607/30–32, 59, 60
See application file for complete search history.

(56) References Cited

U.S. PATENT DOCUMENTS

| | | | |
|---|---|---|---|
| 6,970,070 B2 | 11/2005 | Juels et al. | |
| 7,298,243 B2 | 11/2007 | Juels et al. | |
| 8,515,070 B2 * | 8/2013 | Juels et al. | 380/270 |
| 2001/0048025 A1 * | 12/2001 | Shinn | 235/382 |
| 2002/0120592 A1 * | 8/2002 | Juels et al. | 706/8 |
| 2004/0015207 A1 | 1/2004 | Barriskill et al. | |
| 2004/0222878 A1 | 11/2004 | Juels | |
| 2004/0260363 A1 * | 12/2004 | Arx et al. | 607/60 |
| 2005/0010780 A1 * | 1/2005 | Kane et al. | 713/182 |
| 2005/0065445 A1 | 3/2005 | Arzbaecher et al. | |
| 2006/0022799 A1 | 2/2006 | Juels | |
| 2006/0033608 A1 | 2/2006 | Juels et al. | |
| 2007/0194889 A1 | 8/2007 | Bailey et al. | |
| 2007/0195960 A1 | 8/2007 | Goldman et al. | |
| 2009/0083833 A1 * | 3/2009 | Ziola et al. | 726/2 |
| 2009/0125084 A1 * | 5/2009 | Juels et al. | 607/60 |
| 2010/0185870 A1 * | 7/2010 | Rane et al. | 713/184 |
| 2011/0015693 A1 * | 1/2011 | Williamson | 607/30 |

OTHER PUBLICATIONS

ACES. "H2H: Authentication for Implanted Medical Devices". http://www.aceslab.org/node/1016. Accessed Jan. 31, 2014.*

(Continued)

Primary Examiner — Carl H Layno
Assistant Examiner — Eugene Wu
(74) Attorney, Agent, or Firm — Ryan, Mason & Lewis, LLP

(57) ABSTRACT

An apparatus comprises a medical device configured for implantation into a living organism. The medical device comprises processing circuitry, a memory and interface circuitry configured for communication with a monitoring device. The medical device is configured to receive a request for access from the monitoring device, to measure a physiological value of the living organism, to perform a pairing protocol with the monitoring device, the pairing protocol comprising a secure channel set-up phase followed by an authentication phase, and to permit access by the monitoring device responsive to a successful pairing in accordance with the pairing protocol, the successful pairing being based at least in part on a determination that a physiological value supplied by the monitoring device substantially matches the measured physiological value. The medical device performs the secure channel set-up phase before sending the measured physiological value to the monitoring device.

25 Claims, 6 Drawing Sheets

(56) References Cited

OTHER PUBLICATIONS

Rostami et al. "H2H: Authentication for Implanted Medical Devices". ACM CCS Nov. 4-8, 2013.*
Slides for "H2H: Authentication for Implanted Medical Devices". ACM CCS Nov. 4-8, 2013.*
S-D. Bao et al., "Physiological Signal Based Entity Authentication for the Body Area Sensor Networks and Mobile Healthcare Systems," IEEE 27th Annual International Conference of Engineering in Medicine and Biology Society (EMBS), Sep. 2005, pp. 2455-2458, Shanghai, China.
X. Boyen et al., "Secure Remote Authentication Using Biometric Data," 24th Annual International Conference on the Theory and Applications in Cryptographic Techniques, Advances in Cryptology—Eurocrypt, May 2005, vol. 3494, pp. 147-163., Aarhus, Denmark.
J. Clulow et al., "So Near and Yet So Far: Distance-Bounding Attacks in Wireless Networks," 3rd European Workshop on Security and Privacy in Ad-Hoc and Sensor Networks (ESAS, Sep. 2006), Lecture Notes in Computer Science (LNCS), 2008, pp. 83-97, vol. 4357.
G.I. Davida et al., "On Enabling Secure Applications Through Off-Line Biometric Identification," IEEE Symposium on Privacy and Security, May 1998, pp. 148-157.
Y. Dodis et al., "Robust Fuzzy Extractors and Authenticated Key Agreement from Close Secrets," 26th Annual International Cryptology Conferences, Advances in Cryptology—CRYPTO, Aug. 2006, pp. 18 pages, vol. 4117.
Y. Dodis et al., "Fuzzy Extractors: How to Generate Strong Keys from Biometrics and Other Noisy Data," International Conference on the Theory and Applications of Cryptographic Techniques, Advances in Cryptology—Eurocrypt, May 2004, pp. 523-540, vol. 3027, Interlaken, Switzerland.
K. Fishkin et al., "Some Methods for Privacy in RFIC Communication," 1st European Workshop on Security in Ad-Hoc and Sensor Networks (ESAS), Aug. 2004, pp. 1-13, Heidelberg, Germany.
J. Halamka, M.D. et al., "The Security Implications of VeriChip Cloning," Journal of the American Medical Informatics Association, Technology Evaluation, Nov./Dec. 2006, pp. 601-607, vol. 13, No. 6.
Integrated Medical Devices, Inc., "IMD PSD 410 Pacemaker Produce Overview," http://www.integrated-medical.com/pacemaker.html, 2007, 1 page.
A. Juels et al., "A Fuzzy Vault Scheme," Designs, Codes, and Cryptography, 2006, pp. 237-257, vol. 38, No. 2.
A. Juels et al., "A Fuzzy Commitment Scheme," 6th ACM Conference on Computer and Communications Security (CCS), Nov. 1999, pp. 28-36.
K. Lorincz et al., "Sensor Networks for Emergency Response: Challenges and Opportunities," IEEE Pervasive Computing, Oct.-Dec. 2004, pp. 16-23, vol. 3, No. 4.
C.C.Y. Poon et al., "A Novel Biometrics Method to Secure Wireless Body Area Sensor Networks for Telemedicine and M-Health," IEEE Communications Magazine, Apr. 2006, pp. 73-81, vol. 44, No. 4.
S. Cherukuri et al., "BioSec: A Biometric Based Approach for Securing Communication in Wireless Networks of Biosensors Implanted in the Human Body," 32nd International Conference on Parallel Processing Workshops (ICPPW), Oct. 2003, pp. 432-439, Kaohsiung, Taiwan.
J. Suomalainen et al., "Security Associations in Personal Networks: A Comparative Analysis," 4th European Workshop on Security and Privacy in Ad-Hoc and Sensor Networks (ESAS), Lecture Notes in Computer Science (LNCS), Jul. 2007, pp. 43-57, vol. 4572, Cambridge, United Kingdom.
S.-D. Bao et al., "A Novel Key Distribution of Body Area Networks for Telemedicine," IEEE International Workshop on Biomedical Circuits and Systems, Dec. 2004, pp. S2.1-17-S2.1-20.
"Medical Implant Communication Service (MICS)," FCC 47CFR95.601-95.673 Subpart E/1 Rules for MedRadio Services, Technical Report, Federal Communications Commission, Oct. 2012, pp. 544-564.
Texas Instruments, "Medical Applications Guide," Technical Report, 2010, 153 pages.
A.L. Goldberger et al., "PhysioBank, PhysioToolkit, and PhysioNet: Components of a New Research Resource for Complex Physiologic Signals," Circulation, Jun. 2000, pp. e215-e220, vol. 101, No. 23.
American Heart Association, "Physical Activity and Blood Pressure," http://www.heart.org/HEARTORG/Conditions/HighBloodPressure/PreventionTreatmentofHighBloodPressure/Physical-Activity-and-Blood-Pressure_UCM_301882_Article.jsp, 2012, 5 pages.
S.-D. Bao et al., "Physiological Signal Based Entity Authentication for Body Area Sensor Networks and Mobile Healthcare Systems," IEEE 27th Annual Conference of the Engineering in Medicine and Biology Society (EMBS), Sep. 2005, pp. 2455-2458, Shanghai, China.
S.-D. Bao et al., "Using the Timing Information of Heartbeats as an Entity Identifier to Secure Body Sensor Network," IEEE Transactions on Information Technology in Biomedicine, Nov. 2008, pp. 772-779, vol. 12, No. 6.
E. Barker et al., "Transitions: Recommendation for Transitioning the Use of Cryptographic Algorithms and Key Lengths," Computer Security, NIST Special Publication 800-131A, Jan. 2011, 27 pages.
M. Bellare et al., "Authenticated Key Exchange Secure Against Dictionary Attacks," International Conference on the Theory and Application of Cryptographic Techniques, Advances in Cryptology—EUROCRYPT, May 2000, pp. 139-155, Bruges, Belgium.
S.M. Bellovin et al., "Encrypted Key Exchange: Password-Based Protocols Secure Against Dictionary Attacks," IEEE Computer Society Symposium on Research in Security and Privacy, May 1992, pp. 72-84.
K.A. Brownley et al., "Cardiovascular Psychophysiology," Handbook of Psychophysiology, Second Edition, 2000, pp. 224-264, vol. 2.
S. Cherukuri et al., "BioSec: A Biometric Based Approach for Securing Communication in Wireless Networks of Biosensors Implanted in the Human Body," IEEE International Conference on Parallel Processing Workshops (ICPPW), Oct. 2003, pp. 432-439.
K. Cho et al., "Biometric Based Secure Communications Without Pre-Deployed Key for Biosensor Implanted in Body Sensor Networks," 12th International Workshop on Information Security Applications (WISA), Aug. 2011, 16 pages, Jeju Island, Korea.
B. Danev et al., "On Physical-Layer Identification of Wireless Devices," ACM Computing Surveys (CSUR), Nov. 2012, 31 pages, vol. 45, No. 1, Article No. 6.
T. Drew et al., "Implantable Medical Devices as Agents and Part of Multiagent Systems," 5th International Joint Conference on Autonomous Agents and Multiagent Systems (AAMAS), May 2006, pp. 1534-1541, Hakodate, Hokkaido, Japan.
Kevin Fu, "Inside Risks: Reducing Risks of Implantable Medical Devices," Communications of the ACM, Jun. 2009, pp. 25-27, vol. 52, No. 6.
A.L. Goldberger et al., "Chaos and Fractals in Human Physiology," Scientific American, Feb. 1990, pp. 42-49, vol. 262, No. 2.
S. Gollakota et al., "They Can Hear Your Heartbeats: Non-Invasive Security for Implantable Medical Devices," ACM SIGCOMM, Aug. 2011, pp. 2-13, vol. 41, No. 4, Toronto, Ontario, Canada.
A.J. Greenspon et al., "16-Year Trends in the Infection Burden for Pacemakers and Implantable Cardioverter-Defibrillators in the United States," Journal of the American College of Cardiology, Aug. 2011, pp. 1001-1006, vol. 58, No. 10.
D. Halperin et al., "Pacemakers and Implantable Cardiac Defibrillators: Software Radio Attacks and Zero-Power Defenses," IEEE Symposium on Security and Privacy (SP), May 2008, pp. 129-142.
D. Halperin et al., "Security and Privacy for Implantable Medical Devices," IEEE Pervasive Computing, Jan.-Mar. 2008, pp. 30-39, vol. 7, No. 1.
F. Hu et al., "Trustworthy Data Collection From Implantable Medical Devices Via High-Speed Security Implementation Based on IEEE 1363," IEEE Transactions on Information Technology in Biomedicine, Nov. 2010, pp. 1397-1404, vol. 14, No. 6.
A. Juels et al., "A Fuzzy Vault Scheme," Designs, Codes and Cryptography, Feb. 2006, pp. 237-257, vol. 38, No. 2.

(56) References Cited

OTHER PUBLICATIONS

A. Juels et al., "A Fuzzy Commitment Scheme," 6th ACM Conference on Computer and Communications Security (CCS), Nov. 1999, pp. 28-36, Singapore.

Sharon S. Keller, "NIST-Recommended Random Number Generator Based on ANSI X9.31 Appendix A.2.4 Using the 3-Key Triple DES and AES Algorithms," Technical Report, NIST, Jan. 2005, 4 pages.

M. Kiani et al., "An RFID-Based Closed-Loop Wireless Power Transmission System for Biomedical Applications," IEEE Transactions on Circuits and Systems II: Express Briefs, Apr. 2010, pp. 260-264, vol. 57, No. 4.

William H. Maisel, MD, MPH, "Safety Issues Involving Medical Devices: Implications of Recent Implantable Cardioverter-Defibrillator Malfunctions," Journal of the American Medical Association (JAMA), Aug. 2005, pp. 955-958, vol. 294, No. 8.

M. Meingast et al., "Security and Privacy Issues with Health Care Information Technology," 28th IEEE Engineering in Medicine and Biology Society Conference (EMBS), Aug.-Sep. 2006, pp. 5453-5458.

G.B. Moody et al., "The Impact of the MIT-BIH Arrhythmia Database," IEEE Engineering in Medicine and Biology Magazine, May-Jun. 2001, pp. 45-50, vol. 20, No. 3.

J.H. Nagel et al., "Assessment and Diagnostic Applications of Heart Rate Variability," Biomedical Engineering-Applications, Basis & Communications, Apr. 1993, pp. 147-158, vol. 5.

J. Neyman et al., "On the Problem of the Most Efficient Tests of Statistical Hypotheses," Philosophical Transactions of the Royal Society of London, Series A, Containing Papers of a Mathematical or Physical Character, Jan. 1933, pp. 289-337, vol. 231.

E. Pino et al., "Real-Time ECG Algorithms for Ambulatory Patient Monitoring," American Medical Informatics Association (AMIA) Annual Symposium Proceedings, 2005, pp. 604-608, vol. 2005.

M.-Z. Poh et al., "Non-Contact, Automated Cardiac Pulse Measurements Using Video Imaging and Blind Source Separation," Optics Express, May 2010, pp. 10762-10774, vol. 18, No. 10.

C.C.Y. Poon et al., "A Novel Biometrics Method to Securei Wireless Body Area Sensor Networks for Telemedicine and M-Health," IEEE Communications Magazine, Apr. 2006, pp. 73-81, vol. 44, No. 4.

RSA, "RSA SecurID Authentication in Action: Securing Privileged User Access," Aug. 2007, pp. 1-8.

A. Rukhin et al., "A Statistical Test Suite for Random and Pseudorandom Numbers Generators for Cryptographic Applications," Technical Report, DTIC Document, NIST Special Publication 800-22, May 2001, 164 pages.

M.G. Signorini et al., "Applying Nonlinear Noise Reduction in the Analysis of Heart Rate Variability," IEEE Engineering in Medicine and Biology, Mar.-Apr. 2001, pp. 59-68, vol. 20, No. 2.

F. Stajano et al., "The Resurrecting Duckling: Security Issues for Ad-Hoc Wireless Networks," 7th International Workshop on Security Protocols, Apr. 1999, pp. 172-194, Cambridge, United Kingdom.

K.K. Venkatasubramanian et al., "Physiological Value-Based Efficient Usable Security Solutions for Body Sensor Networks," ACM Transactions on Sensor Networks, Jul. 2010, pp. 1-36, vol. 6, No. 4, Article 31.

S. Warren et al., "Interoperability and Security in Wireless Body Area Network Infrastructures," IEEE 27th Annual Conference on Engineering in Medicine and Biology Society, Sep. 2005, 4 pages, Shanghai, China.

F. Xu et al., "IMDGuard: Securing Implantable Medical Devices with the External Wearable Guardian," IEEE INFOCOM, Apr. 2011, pp. 1862-1870.

R. Yulmetyev et al., "Quantification of Heart Rate Variability by Discrete Nonstationary Non-Markov Stochastic Processes," Physical Review E—Statistical, Nonlinear, and Soft Matter Physics, Apr. 2002, pp. 1-15, vol. 65, No. 4, Part 2A.

Z. Albus et al., "Ultra-Low Power Comparison: MSP430 vs. Microchip XLP Tech Brief," Technical Report, White Paper, 2009, 10 pages.

\* cited by examiner

FIG. 8

Algorithm 1 Neyman-Pearson threshold $Th$ computation

Inputs: $n$, $\{e_i\}_{i=1}^{4}$, $FN_{Req}$
Outputs: $Th$, $FP$ $P[1:n+1] \leftarrow \text{binomial}(n, 0.5)$;
for $i = 1$ to $4$ do
    $Q[1:n+1][i] \leftarrow \text{binomial}(n, e_i)$
end for
$j = 1$;
for $\vec{u} = \langle u_1, u_2, u_3, u_4 \rangle \in (\mathbb{Z}_n)^4$ do
$$M[j][1] = \prod_{i=1}^{4} P[u_i];$$
$$M[j][2] = \prod_{i=1}^{4} Q[u_i][i];$$
$$M[j][3] = \log\left(\frac{M[j][1]}{M[j][2]}\right);$$
    $j \leftarrow j + 1$
end for
sort $M$ on $M[\cdot][3]$ (Column 3);
$p \leftarrow 0$; $j \leftarrow 0$
while $p \leq FN_{Req}$ do
    $j \leftarrow j + 1$;
    $p \leftarrow p + M[j][2]$
end while
$\tau \leftarrow j - 1$;
if $\tau < 1$ then output $\perp$; halt
end if
$$FP \leftarrow \sum_{k=1}^{\tau} M[k][1];$$
$Th \leftarrow M[\tau][3]$

AUTHENTICATION OF EXTERNAL DEVICES TO IMPLANTABLE MEDICAL DEVICES USING BIOMETRIC MEASUREMENTS

FIELD

The present invention relates generally to medical devices, and more particularly to authentication of external devices to medical devices that are implantable in humans or other living organisms.

BACKGROUND

Implantable medical devices (IMDs) apply continuous monitoring and automatic therapies for the treatment of chronic medical disorders. IMDs may be implemented partially or fully in patients' bodies, and are often sophisticated devices containing batteries, embedded CPUs, sensors, and actuators. In recent years, IMDs have been used to treat a broadening range of disorders, and thus their use is growing. An example of an IMD is an implantable cardioverter defibrillator (ICD), which can detect dangerously rapid heart rhythms and administer an electric shock to restore normal cardiac activity. Other IMDs include pacemakers, neurostimulators and implantable drug pumps.

IMDs generally contain radios for communication with external devices, or programmers. Programmers can reprogram IMDs and extract patient data from them. Such wireless communication permits safe, non-invasive access to IMDs. Wireless communication, however, brings security risks of embedded computing into the human body. For example, attackers can exploit design flaws in common IMDs to seize unauthorized control and potentially harm victims as well as expose privacy-sensitive data.

At the same time, IMDs must allow rapid, unimpeded access by medical personnel. A patient's life may depend on the ability of first responders to gain swift access to his or her IMDs. An access-control system that requires emergency medical technicians to reference a secure database, obtain a password from the patient, or access a patient's wallet or handbag poses a threat to timely medical intervention.

It is apparent from the foregoing that a strong tension exists between the requirements of IMD security and IMD accessibility. What is needed is an approach that achieves a suitable balance between these competing requirements. Conventional techniques fail to provide adequate solutions for authentication of external devices to IMDs. Techniques for providing a solution to the problem of emergency access to IMDs are discussed in U.S. patent application Ser. No. 12/251,036, entitled "Access Control for Implanted Medical Devices", which is commonly assigned herewith and incorporated by reference herein. Although some progress has been made, further improvements are required to adequately address the above-noted problems of access to IMDS.

SUMMARY

Illustrative embodiments of the present invention provide techniques for securing access to IMDs from a monitoring device.

In one embodiment, an apparatus comprises a medical device configured for implantation into a living organism. The medical device comprises processing circuitry, a memory and interface circuitry configured for communication with a monitoring device. The medical device is configured to receive a request for access from the monitoring device, to measure a physiological value of the living organism, to perform a pairing protocol with the monitoring device, the pairing protocol comprising a secure channel set-up phase followed by an authentication phase, and to permit access by the monitoring device responsive to a successful pairing in accordance with the pairing protocol, the successful pairing being based at least in part on a determination that a physiological value supplied by the monitoring device substantially matches the measured physiological value. The medical device performs the secure channel set-up phase before sending the measured physiological value to the monitoring device.

Advantageously, one or more of the illustrative embodiments disclosed herein provide simple and efficient techniques for providing enhanced security in IMD devices, in a manner that achieves a suitable balance between the competing requirements of security and accessibility.

These and other features and advantages of embodiments of the present invention will become more readily apparent from the accompanying drawings and the following detailed description.

BRIEF DESCRIPTION OF THE DRAWINGS

FIG. 8 illustrates pseudocode for generating a threshold value, according to an embodiment of the invention.

DETAILED DESCRIPTION

The present invention will be described herein with reference to an exemplary IMD system in which multiple IMDs communicate with a medical monitor. It is to be appreciated, however, that the invention is not restricted to use in this or any other particular IMD system configuration.

The term "IMD" as used herein is intended to include, for example, an RFID tag or any other type of implantable or implanted medical device configurable for wireless communication with one or more external monitors.

The terms "monitor" or "monitoring device" as used herein are intended to include, for example, an RFID tag reader or any other type of device capable of interacting with an IMD so as to receive medical information or other information from the IMD. Monitoring devices may therefore include, again by way of example, devices that receive physiological values by radio from IMDs, as well as devices that are able to reprogram or otherwise control IMDs.

Figure 1:
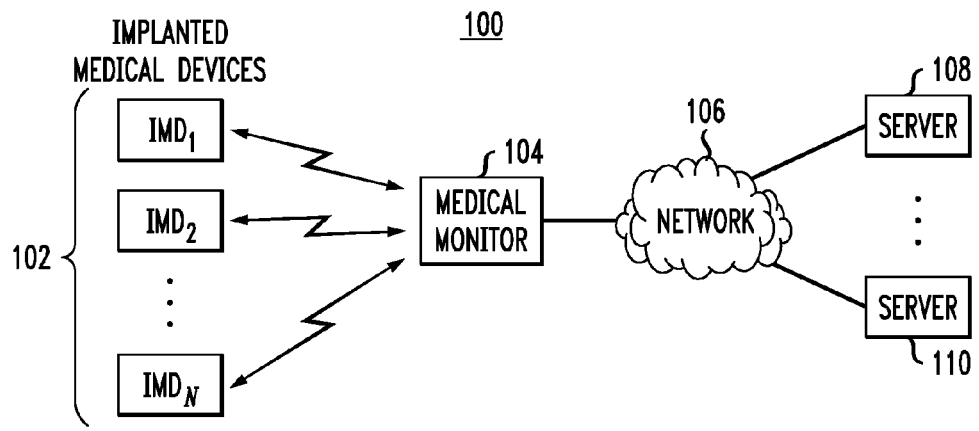
FIG. 1 is a simplified block diagram of an exemplary IMD system, according to an embodiment of the invention.

FIG. 1 shows an IMD system 100 in which the present invention may be implemented. The system 100 includes a number N of IMDs 102, more particularly denoted by their associated identifiers $IMD_1, IMD_2, \ldots IMD_N$, and a medical monitor 104. The monitor 104 communicates with the IMDs 102 and receives medical information therefrom. Such information may include, for example, one or more transmitted identifiers, diagnostic data, measured physiological values, etc. The monitor 104 is coupled via a network 106 to servers denoted 108, 110. Although not explicitly shown in FIG. 1, a verifier may be associated with the monitor 104. Such a verifier may be implemented, for example, using one or both of the servers 108, 110, another network element accessible via the network 106, or another system element coupled to or otherwise associated with the monitor 104.

The IMDs 102 are each configured for implantation into a living organism, such as a human being. The IMDs may each be implanted in a separate living organism, or multiple such IMDs may be implanted in each of one or more living organisms. Such organisms are omitted from the figure for simplicity and clarity of illustration. The medical monitor 104 is typically arranged external to the living organism(s).

A given IMD 102 in accordance with the invention generally includes circuitry comprising memory, processing logic and a radio frequency (RF) transceiver. These elements may be configured in a manner similar to that used in conventional IMDs.

As indicated above, one or more of the IMDs 102 may comprise respective RFID tags. A conventional RFID tag typically comprises an integrated circuit transceiver capable of transmitting information to a nearby reader in response to a query from the reader. Many RFID tags are "passive" in that they do not include a battery or other power source, but instead obtain the power necessary to operate from the query signal itself.

Additional details regarding illustrative RFID systems that may be utilized in implementing aspects of the present invention can be found in, for example, U.S. Pat. No. 6,970,070 entitled "Method and Apparatus for Selective Blocking of Radio Frequency Identification Devices," U.S. Pat. No. 7,532,104 entitled "Low-Complexity Cryptographic Techniques for use with Radio Frequency Identification Devices," U.S. Pat. No. 7,298,243 entitled "Radio Frequency Identification System with Privacy Policy Implementation based on Device Classification," U.S. Pat. No. 7,750,793 entitled "Methods and Apparatus for RFID Device Authentication," U.S. Pat. No. 7,920,050 entitled "Proxy Device for Enhanced Privacy in an RFID System," and U.S. patent application Ser. No. 11/671,275, filed Feb. 5, 2007 and entitled "Security Provision in Standards-Compliant RFID Systems," all of which are commonly assigned herewith and incorporated by reference herein.

It is to be appreciated, however, that the IMDs 102 need not be implemented as RFID tags. Any of a wide variety of medical devices capable of communicating with external monitoring devices may be used.

The network 106 may represent a global computer network such as the Internet, a wide area network (WAN), a local area network (LAN), a satellite network, a telephone or cable network, or various portions or combinations of these and other types of networks. The servers 108, 110 may be conventional processor-based information processing devices of a type conventionally utilized in conjunction with IMD monitors in an IMD system.

The particular number N of IMDs 102 in the system 100 is purely arbitrary, and the system can be configured to support any desired number of such devices. Also, although only a single monitor 104 is shown in the figure for simplicity and clarity of illustration, the system may include multiple monitors. Furthermore, it should be noted that a given monitor need not be connected to a network, and may instead operate as a stand-alone device, or may be only intermittently connected to the network. Also, a given monitor can be directly connected to a server or other system element, rather than connected thereto over a network as illustrated in the example system 100.

Figure 2:
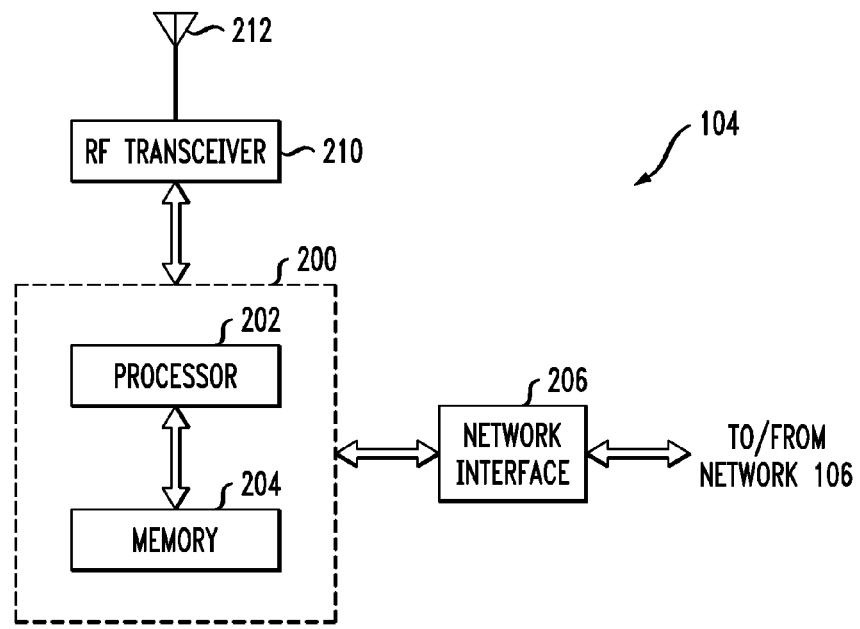
FIG. 2 illustrates one possible implementation of a medical monitor, according to an embodiment of the invention.

FIG. 2 shows one possible implementation of the medical monitor 104 of the FIG. 1 system. Such a medical monitor is an example of what is more generally referred to herein as a "monitoring device." The medical monitor in this implementation includes a processing block 200, comprising a processor 202 coupled to a memory 204, a network interface 206, an RF transceiver 210, and an antenna 212. One or more of these elements may be implemented in whole or in part as a conventional microprocessor, digital signal processor, application-specific integrated circuit (ASIC) or other type of circuitry, as well as portions or combinations of such circuitry elements. Software programs for controlling the operation of the monitor 104 may be stored in the memory 204 and executed by the processor 202. The memory 204, and other memories referred to herein, may comprise, for example, random access memory (RAM), read-only memory (ROM), electrically erasable programmable ROM (EEPROM), or other types of storage elements, in any combination.

The medical monitor 104 may be implemented in or otherwise comprise at least a portion of a mobile telephone, a portable computer, a personal digital assistant (PDA), a hardware-based authentication token such as an RSA SecurID® token, or any other type of processing device utilizable in communicating with an IMD as described herein. The invention thus does not require any particular monitoring device configuration.

Figure 3:
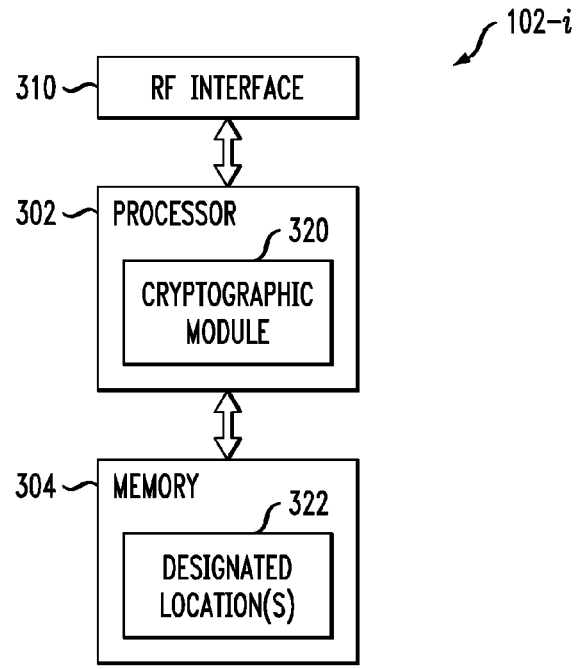
FIG. 3 illustrates one possible implementation of an IMD, according to an embodiment of the invention.

FIG. 3 shows one possible implementation of a given one of the IMDs 102-*i* of the FIG. 1 system. The IMD 102-*i* comprises a processor 302 coupled to a memory 304, and an RF interface 310 which may comprise, for example, an RF transceiver and an associated antenna. The processor may be in the form of relatively simple processing logic, or may represent a more complex processor. In the implementation shown, the processor 302 implements a cryptographic module 320, which may comprise, for example, an encryption engine, a fuzzy extractor, or other processing element(s) providing cryptographic functionality. The cryptographic module may comprise one or more software programs that are stored in memory 304 and executed by processor 302. It is important to note, however, that embodiments of the invention do not require the use of cryptographic module 320.

The memory 304 comprises one or more designated locations 322, which may be accessible to both the IMD 102-*i* and to the monitor 104. The monitor may be required to submit a personal identification number (PIN) or other authentication information in order to access the designated locations 322. The designated locations 322 may comprise substantially the entire memory of the IMD 102-*i*, or just a designated subset of the IMD memory. For example, the memory 304 may be organized in the form of multiple banks, with one or more of the banks being designated as accessible to the monitor 104.

The memories 204 and 304 are examples of what are more generally referred to herein as processor-readable storage media. Other examples of such media that may be used to store software programs for use in implementing the present invention include computer disks, storage drives, etc.

Figure 4:
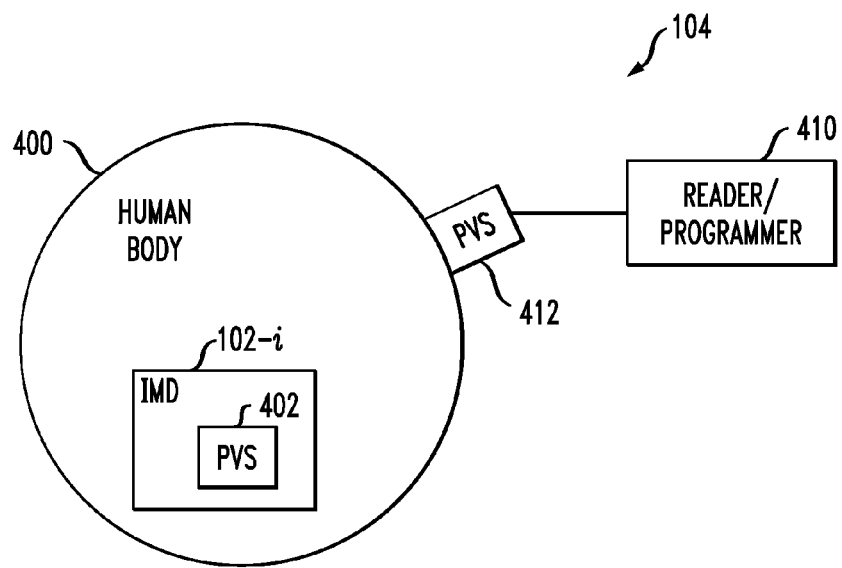
FIG. 4 shows a more detailed view of a portion of the IMD system of FIG. 1, according to an embodiment of the invention.

Referring now to FIG. 4, it can be seen that a given IMD 102-*i* is implanted into human body 400. The IMD 102-*i* comprises a physiological value (PV) sensor (PVS) 402. The monitoring device 104 in this embodiment comprises a reader/programmer 410 and a PVS 412. The reader/programmer, which may comprise a reader, a programmer or both, is coupled to the PVS 412. The IMD 102-*i* and the monitoring device 104 use their respective PVS elements 402, 412 to measure PVs of the human body 400. In addition, while various embodiments are described below with respect to IMDs implanted into a human body, embodiments of the invention can also be used with IMDs implanted in various other living organisms.

Embodiments of the invention implement an access-control policy referred to herein as "touch-to-access." A programmer, such as the operator of a monitoring device 104, obtains access to a given IMD 102-$i$ if and only if it has significant physical contact with the living organism in which the given IMD 102-$i$ is implanted. The description "if and only if" above refers to a desired degree of certainty for false positives and/or false negatives as will be detailed below. The touch-to-access control policy can thus be said to have forward security such that authentication to an IMD lapses once the monitoring device loses physical contact with the living organism. Touch-to-access offers a practical and effective balance between the competing access requirements of permissiveness in emergencies and resistance to attacks.

Embodiments of the invention which implement the touch-to-access policy use a time-varying biometric, also referred to as a PV. When monitoring device 104 seeks access to an IMD 102-$i$, the monitoring device 104 initiates an authentication session. The IMD 102-$i$ takes a reading $\alpha$ of the PV and at the same time, the monitoring device 104 takes its own reading $\beta$. If $\beta$ is "nearly equal" to $\alpha$, then the monitoring device 104 obtains access to the IMD 102-$i$. PV readings are noisy, and thus near equality is used in place of an exact equality.

The touch-to-access policy can in principle rely on any PV. In some embodiments, the touch-to-access policy uses the waveform produced by a heart, known as an electrocardiogram (ECG). Embodiments which use an ECG as the PV are referred to herein as heart-to-heart (H2H) systems. It is important to note, however, that embodiments of the invention are not limited solely to arrangements where the PV is an ECG, and that various embodiments described below with respect to H2H systems can be adapted for use with various other PVs. There are many other PVs that are time-varying and thus suitable for use as a dynamic biometric. These include, by way of example, inter-pulse interval (IPI), heart rate variance (HRV), photoplethysmograms (PPG), brainwaves, etc. It should be noted that an IMD system in accordance with the invention can supplement its dynamic biometrics based on PVs with conventional static biometrics such as fingerprints or retina scans.

H2H systems are well suited for authentication to cardiac IMDs such as ICDs and pacemakers, which are among the most widely used IMDs today. H2H systems, however, can work with various IMDs equipped to measure ECG anywhere in a human body, not just cardiac devices. Suitably processed ECG samples effectively constitute a low-bandwidth stream of random bits well suited for forward-secure authentication. In H2H systems, a monitoring device 104 and an IMD 102-$i$ take independent, time-synchronous ECG readings. The IMD 102-$i$ compares the two results to enforce a touch-to-access policy.

The design of H2H systems raises a number of technical challenges. The first is to ensure that the statistical properties of ECG measurements are such that they are a suitable PV for authentication. H2H derives a key source from a sequence of key bits that serve to authenticate the monitoring device 104 to the given IMD 102-$i$. Secure touch-to-access authentication requires that the key source have certain statistical properties, ideally that it be truly random, meaning that its constituent bits have high entropy and are statistically independent. The key source is then hard for an attacker to guess without physical access to the patient and also ensures forward-security in H2H systems, i.e., that old key source bits don't reveal future ones.

The inventors have analyzed real patient ECG data and have found that it is possible, with a reasonable degree of error, to extract four truly random and statistically uncorrelated bits from the ECG wave corresponding to a single heartbeat. When collected over a period of time, the ECG signal can be used to provide strong authentication of a monitoring device 104. For example, collection over a 47-second interval can ensure authentication of a monitoring device 104 with a false acceptance rate of about $1.2 \times 10^{-8}$ and a false rejection rate of $10^{-4}$. H2H systems also use an optimal Neyman-Pearson scheme for testing PV validity, i.e., testing $\alpha \approx \beta$.

Statistical properties alone do not ensure that ECG signals may be used to enforce touch-to-access policies in H2H systems. Recently developed systems can read cardiac rhythms remotely via videocamera, and even accurately measure a patient's pulse by measuring skin color changes, which vary subtly with cardiac rhythms. The best of such video systems, however, do not reveal statistically significant information about an ECG key source used in H2H systems as will be described below.

Readings $\alpha$ and $\beta$ of the key source PV can be noisy, which presents another challenge for H2H systems. A valid monitoring device 104 can obtain a PV $\beta \approx \alpha$ without achieving exact equality $\beta = \alpha$. Many cryptographic tools such as password-authenticated key agreement require exact equality, while many error-tolerant cryptographic tools can needlessly sacrifice entropy. Yet another challenge in implementing H2H systems is the tight computational and power constraints of IMDs. Conventional microcontrollers commonly used in IMDs today, such as the Texas Instruments (TI) MSP430, can perform only lightweight cryptography. IMDs are long-lived devices, often averaging a five-to-seven year lifetime. Battery replacement typically requires surgical intervention or other invasive procedures, and thus power conservation is essential. H2H systems can protect new IMDs as well as legacy in-vivo IMDs with upgradable firmware as long as the particular implementation of H2H meets the IMD's limited memory and computational resources.

Embodiments of the invention utilize a pairing protocol which exploits the fact that key source bits in ECG signals are statistically uncorrelated. Thus, $\alpha$ and $\beta$ can be treated as one-time authentication values. H2H systems require only a low-exponent RSA encryption (tens of modular multiplications) and a few advanced encryption standard (AES) invocations and hash computations by the IMD.

Before turning to the details of H2H systems, a brief discussion of the ECG statistical model is provided. An ECG waveform has a number of physiologically significant features. The R-peak is the most prominent feature of an ECG waveform, and corresponds to the "beat" in a heartbeat. The time between two consecutive R-peaks, or the heartbeat duration, is commonly referred to as the inter-pulse interval (IPI). A typical ECG cycle includes other physiologically significant, named features: The P-wave, which occurs before the R-peak, the QRS complex, which includes sharp valleys before and after the R-peak, denoted by Q and S respectively, and the T-wave, following the S valley.

The heart rhythm is governed by the parasympathetic nervous system, which includes many non-linearly interacting processes to give the IPI its chaotic nature. The ECG waveform, and parasympathetic network more generally, are influenced by both long-term trends such as circadian rhythm and short-term temperature and respiratory changes. Thus ECG waves simultaneously exhibit both long term patterns and short-term chaotic behavior.

The ECG signal is well modeled as a stochastic process. The existence of long-term patterns renders the process non-stationary, meaning that the parameters of its underlying distribution, e.g., mean and variance, fluctuate over time. We introduce transforms for H2H systems, however, that eliminate long-term variations, creating a residual signal that is well-approximated by a wide-sense stationary stochastic process, i.e., one whose first and second moments don't change over time. There is a strongly random element in IPI time series values, and as such IPIs are a natural source of randomness.

In embodiments of H2H, four high-grade random bits are extracted per IPI from the ECG signal, i.e., bits that have maximal entropy and are fully uncorrelated. This entropy measure can be used to characterize the security of H2H systems. H2H systems quantify and use different error rates incurred by individual high-grade random bits using a Neyman-Pearson approach. This approach provides significant advantages relative to techniques which assign the same significance to all random bits. H2H systems thus enable authentication with an optimal false positive rate for a given false negative constraint.

H2H systems may be used in a variety of contexts. For example, H2H systems are well suited for use in emergency authentication, when medical personnel, e.g., emergency medical technicians (EMTs), need access to a given IMD 102-$i$, but have no pre-established keys or trust relationship. Rapid and reliable access to the IMD 102-$i$ is important. Thus H2H looks to make efficient use of PV randomness, so that authentication can proceed quickly.

H2H systems assume and thus do not require public-key infrastructure (PKI) for certification of trustworthy monitoring devices and programmers. The challenges of key revocation, tamperproofing of programmers to prevent key compromise, etc., are substantial. Similarly, H2H systems assume and thus do not require an authority which may be contacted on the fly for access credentials, as it would often be impractical for medical personnel to use such an authority. In addition, such an authority requires an infrastructure of broad and robust trust relationships. H2H systems can thus rely solely on touch-to-access policy for authentication.

Embodiments of the invention, however, are not limited solely to use with the touch-to-access authentication, and may instead use PKI or on the fly credential lookup to supplement authentication. For example, in non-emergency situations such as when a patient is receiving routine medical care, it may be practical for medical personnel to retrieve device-specific keys. But in unusual situations, e.g., patients traveling abroad, lost keys, and so forth, H2H systems are useful as a secondary or backup authentication mechanism.

The ECG waveform goes flat when an acute heart attack occurs. Similarly, in some late-stage terminal diseases, the parasympathetic network collapses and as a result, the ECG waveform loses most of its entropy. The hugely distorted ECG waveform resulting from such conditions is readily identifiable. In such cases, H2H systems are designed to enter a promiscuous mode in which any monitoring device or programmer may access the given IMD 102-$i$. For these acute events, the risks of medical failure greatly outweigh those of malicious attack. Additionally, these extreme medical conditions occur rarely.

Embodiments of H2H systems are discussed with respect to a model adversary. The adversary is modeled as an attacker present during an authentication session between a monitoring device 104 and a given IMD 102-$i$. The adversary is assumed to have complete network control, i.e., has the ability to drop (jam), modify, replay and forge messages at will. Protection against strong, active adversaries in a pairing protocol presents a significant obstacle to overcome. As will be detailed below, embodiments of the H2H system provide improved protection again man-in-the-middle attacks and other adversary attacks.

Figure 5:
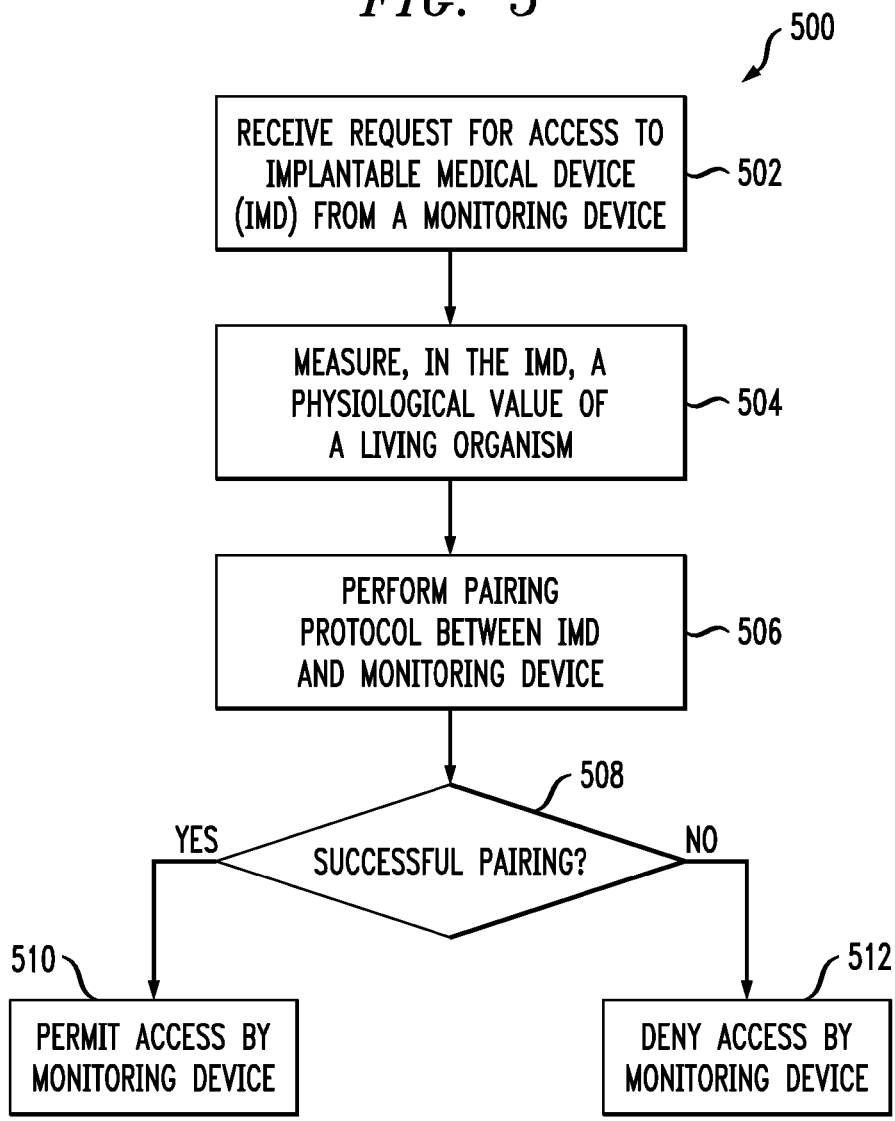
FIG. 5 is a flow diagram showing portions of an access control protocol, according to an embodiment of the invention.

FIG. 5 illustrates an access control protocol 500. Initially, a request for access to an IMD such as IMD 102-$i$ is received 502 from a monitoring device such as monitoring device 104. In step 504, the IMD 102-$i$ measures a physiological value, a, of the living organism in which it is implanted. Next a pairing protocol is performed 506 between the IMD 102-$i$ and the monitoring device 104. A determination is made in step 508 as to whether the pairing protocol results in a successful pairing. If a successful pairing is made, the IMD 102-$i$ will permit 510 the request for access by the monitoring device 104. If a successful pairing is not made, the IMD 102-$i$ will deny 512 the request for access by the monitoring device 104.

As discussed above, a number of uncorrelated random bits may be extracted from IPIs, which may form the basis of a key. An approach which simply utilizes a portion of the quantized IPIs for key derivation and concatenating the three or four least significant bits of the quantized IPIs to generate the key does not provide optimal security. Such approaches rely on a measure of the Hamming distance between keys generated by two parties for authentication. Authentication is successful is if the Hamming distance between the keys is below a predefined threshold value. Analysis of ECG measurements shows that the four least significant bits of IPIs are independent and identically distributed (i.i.d.). This characteristic may be illustrated by application of the National Institute of Standards and Technology (NIST) suite of statistical tests to a dataset of ECG measurements. The lack of correlation between bits allows the use of a simple Hamming distance metric to compare received and measured bits. Embodiments of the invention, however, can further characterize the error rate difference among bits, or the amount of noise that distorts bits derived from a PV reading such as an IPI. The error rate can thus be defined as the probability, for a given IPI-derived bit, that two devices, e.g., the monitoring device 104 and the IMD 102-$i$, read the same IPI at different points on the body but output differing bit values. Analysis of datasets of ECG measurements shows that the error rates vary considerably across quantized bits. There is an inverse relationship between the significance of a bit and its error rate and entropy.

Using individual error rates for each bit, H2H systems can quantify the probability that a monitoring device 104 has physical contact with the living organism. It is convenient to treat the PV $\alpha$ measured by the IMD 102-$i$ as correct. Error rates then characterize honest or attacker deviation from a.

In some embodiments of H2H, a PV includes only the four least significant bits of an IPI, collectively denoted $IPI_4$. It is important to note, however, that embodiments of the invention may use more or less than the four least significant bits of an IPI in a PV. The bits in $IPI_4$ are i.i.d. variables. Thus, an adversary that hasn't made skin contact with a victim, and has no information about IPIs, can at best guess an $IPI_4$ value by assigning random values to each of its constituent bits. Suppose that n is the number of distinct $IPI_4$ instances read in an H2H authentication session. Then the total number of incorrect guesses by an adversary, Adv, for any given one of the four $IPI_4$ bit positions can be modeled as a binomial distribution with Bernoulli trial probability of 0.5, denoted by $B(n, 0.5)$.

The total number of incorrect bit outputs for a given bit position i by a valid monitoring device 104 with skin contact can be modeled by another binomial distribution $B(n,e_i)$, where $e_i$ is the error rate of bit $i \in \{1, 2, 3, 4\}$. The bit position i is distinct from the i used to represent IMD 102-i. The error rate values, as discussed above, may be obtained from an analysis of a dataset of ECG measurements. An adversary thus produces significantly more errors than a valid monitoring device in each bit position.

H2H systems determine whether $\alpha \approx \beta$, where the IMD 102-i reads PV $\alpha$ and the monitoring device reads PV $\beta$. The determination of whether the PV $\beta$ is authentic, i.e., resulting from skin contact, may be viewed as a hypothesis test. The underlying hypothesis is that the monitoring device 104's claimed or supplied PV $\beta$ is drawn from the probability distribution of an honest programmer instead of an adversary's guessing distribution.

Embodiments of H2H use a Neyman-Pearson hypothesis test to distinguish between honest and adversarial authentication attempts. Let the error value u denote the set of errors in $\beta$, i.e., bit positions that differ from $\alpha$. Neyman-Pearson states that for a given maximum acceptable false negative rate, the false positive rate is minimized as follows. For a fixed threshold value Th, whose computation is discussed below, a supplied value $\beta$ is accepted as valid when the following criterion holds:

$$\log\left(\frac{P(u)}{Q(u)}\right) > Th \quad (1)$$

where P(u) denotes the probability of an adversary with no physical contact with the living organism yielding error value u and Q(u) denotes the probability of a valid monitoring device 104 yielding error value u. Distributions P(u) and Q(u) may be modeled according to the binomial distributions discussed above.

As the bits in a given bit position i are i.i.d., the correctness of a PV is invariant to which $IPI_4$ values contain erroneous bits. The authenticity of PV $\beta$ can thus be determined based only on the total number of correct or incorrect values in each bit position. We can treat u as an equivalence class of PVs. It is convenient to regard u as a vector $\vec{u} = <u_1, u_2, u_3, u_4>$, where $u_i$ denotes the total number of IPIs in $\beta$ that are incorrect in bit position i (that differ from those in $\alpha$). Now, $P(\vec{u}) = \Pi_{i=1}^{4} P_i(u_i)$ and $Q(\vec{u}) = \Pi_{i=1}^{4} Q_i(u_i)$, where $P_i(u_i)$ and $Q_i(u_i)$ denote the probability of a total of $u_i$ incorrect IPI values for bit position i in adversarial and honest scenarios, respectively. It follows that $$\log\left(\frac{P(\vec{u})}{Q(\vec{u})}\right) = \sum_{i=1}^{4} \log(P_i(u_i)) - \sum_{i=1}^{4} \log(Q_i(u_i)). \quad (2)$$

Based on Equation 2, complete, compact representations of $P(\vec{u})$ and $Q(\vec{u})$ can be constructed. For a given value of n, it suffices to build a table containing $\log(P_i(u_i))$ and $\log(Q_i(u_i))$ for $i \in \{1, 2, 3, 4\}$ and $u_i \in \mathbb{Z}_n$. Because the error rate of the adversary is ½ for all bit positions, $Q_i(u_i) = Q_j(u_j)$ for any $i, j \in \{1, 2, 3, 4\}$. Thus, it suffices to store $\log(Q_i(u_i))$ values for i=1 only. Consequently, a full table contains just $(4+1) \times (n+1) = 5n+5$ values. Given such a table, performing the Neyman-Pearson test in Equation 1 requires just $(4+1)=5$ table lookups, eight additions, and one subtraction. Thus, embodiments of H2H can fit within tight computational restraints of various IMDs as discussed above. This computation is performed during authentication.

The Neyman-Pearson hypothesis states the existing of threshold Th, but does not specify how to compute Th. An algorithm for determining Th is presented in FIG. 8. The space $(\mathbb{Z}_n)^4$ of possible values of $\vec{u}$ is relatively small. Embodiments of H2H can use $n \leq 50$ for sufficient strength of authentication, meaning that the total number of possible values of $\vec{u}$ is at most $50^4 = 6,250,000$. Consequently, Th may be computed using a brute force algorithm. The psuedocode of FIG. 8 computes Th for a target false-negative rate $FN_{Req}$. It first constructs a matrix $M[n^4][3]$ with $n^4$ rows, one for each $\vec{u} \in (\mathbb{Z}_n)^4$, and three columns. For each row $\vec{u}$, Column 1 contains $P(\vec{u})$, Column 2 contains $Q(\vec{u})$ and Column 3 contains $$\log\frac{P(\vec{u})}{Q(\vec{u})}.$$

The rows of M are sorted in ascending order with respect to Column 3 values. Then, from top (smallest) to bottom (largest), Column 1 values are accumulated in a variable p until the lowest row $\tau$ is reached for which the cumulative value $p \leq FN_{Req}$. The Column 3 value of row $\tau$, namely $M[\tau][3]$, is the optimum threshold value Th. By summing Column 2 values over the first $\tau$ rows, we also obtain the corresponding false-positive rate (FP). A computation failure outputs special symbol $\perp$.

The dominant cost of the algorithm of FIG. 8 is sorting. Thus its asympototic complexity is $O(n^4 \log n)$. In practice, as n is small, the algorithm executes quickly. The algorithm of FIG. 8, however, may be precomputed offline and thus the IMD 102-i is not required to perform the algorithm of FIG. 8 to determine threshold Th.

In one embodiment of H2H, the false negative rate $FN_{Req}$ is chosen as $10^{-4}$. In practical terms, this means that a monitoring device 104 without physical contact to the living organism would fail on average in one in every 10,000 attempts and it would fail twice consecutively at most once in every one hundred million attempts. Various other false negative rates may be chosen as desired for a particular application. There is a tradeoff between the false negative rate and the false positive rate for varying numbers n of $IPI_4$ values used in authentication. The lower the false negative rate, the higher the false positive rate. In addition to choosing a particular false negative rate, the other key parameter of an H2H system is the number n of $IPI_4$ values measured for authentication. As n grows, so does the ECG measurement time required for authentication in an H2H system.

In one embodiment, n is set equal to 47. Given the false negative rate $FN_{Req}$ of $10^{-4}$, the corresponding false positive rate is $FP=1.2 \times 10^{-8}$. This false positive rate shows the feasibility of a strong level of authentication. As a point of comparison, this false positive rate is lower than the false acceptance rate of a typical eight-digit RSA SecurID® token. Since the average resting heart rate of a human is 60-80 beats per minute, the recording time for n=47 would on average take between 35 to 47 seconds. In other embodiments a lower or higher false negative rate, and thus a lower or higher measurement time, may be used.

An adversary, however, can make multiple attempts to gain access to an IMD 102-i or a monitoring device 104. The success probability of such attacks relative to the false positive rate will be detailed below. Exponential backoff in the IMD 102-*i* can be used as a countermeasure to such attacks.

One approach to authentication could work as follows. A monitoring device 104 establishes a secure connection with the IMD 102-*i*. The IMD 102-*i* and the monitoring device 104 then take respective PV readings α and β. The monitoring device then transmits β to the IMD 102-*i*. If β≈α, i.e., β is close to α, the IMD 102-*i* accepts the monitoring device as valid. This approach, however, is vulnerable to a man-in-the-middle attack. An adversary Adv can simultaneously pose as the IMD 102-*i* in a session with the monitoring device 104 and as the monitoring device 104 in a session with the IMD 102-*i*. On receiving β from the monitoring device 104, the Adv forwards it to the IMD 102-*i*, resulting in a successful authentication.

Password-authenticated key-exchange (PAKE) schemes are designed to address such attacks. The PVs α and β measured respectively by the IMD 102-*i* and the monitoring device 104 may be treated as passwords: the monitoring device 104 gains access to the IMD 102-*i* by demonstrating its approximate knowledge of "password" α, i.e., that it knows β such that α≈β. PAKE schemes, however, have two drawbacks. First, due to read errors, the IMD 102-*i* checks for approximate equality, i.e., α≈β. PAKE, however, requires exact equality. More involved approaches, e.g., bit-by-bit password testing, or use of fuzzy extraction techniques, can convert PAKE into a "fuzzy" tool for approximate equality testing. These techniques, however present the problem of computational cost. A single PAKE execution requires more computation and energy expenditure than is typically desirable on IMDs, which are highly constrained in terms of power and computational resources. A "fuzzy" PAKE would require even more computation.

Figure 6:
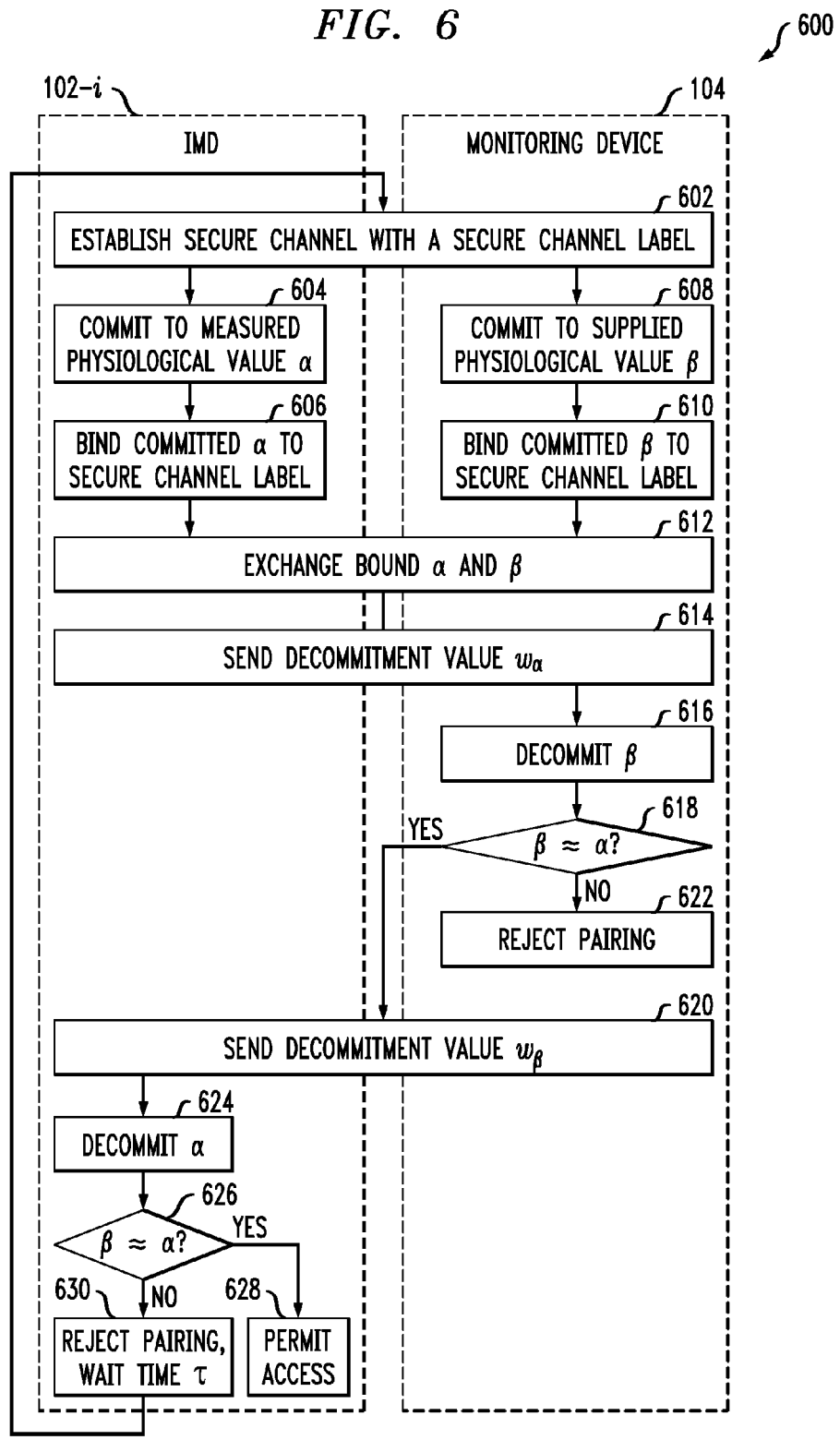
FIG. 6 is a flow diagram showing portions of a pairing protocol, according to an embodiment of the invention.

FIG. 6 illustrates a pairing protocol 600 which may be carried out in embodiments of the invention. In step 602, the IMD 102-*i* and the monitoring device 104 can establish a secure channel with a secure channel label. Next, in steps 604 and 606, the IMD 102-*i* commits to a measured physiological value a and binds the committed α to the secure channel label determined in step 602. In steps 608 and 610, the monitoring device 104 commits to a supplied physiological value β and binds the committed β to the secure channel label determined in step 602. In step 612, the IMD 102-*i* and the monitoring device 104 exchange the bound, committed values. The IMD 102-*i* then sends 614 a decommitment value $w_\alpha$ to the monitoring device 104. The monitoring device 104 decommits β in step 616, and determines 618 whether β≈α. If β≈α, the monitoring device 104 sends 620 decommitment value $w_\beta$ to IMD 102-*i*, otherwise the monitoring device 104 rejects 622 the pairing. The IMD 102-*i* then decommits 624 α. In step 626, the IMD 102-*i* determines whether α≈α. If α≈β, the IMD 102-*i* permits 628 access by the monitoring device 104, otherwise the IMD 102-*i* rejects 630 the pairing and waits a time τ before accepting a new request for access.

A more specific example of a pairing protocol will now be described with respect to FIG. 7. Since α and β in H2H systems may be considered one-time values, fresh readings may be used to authenticate every session since the readings are statistically independent across time. Consequently, it is possible to reveal α and β safely at the end of an authentication protocol, which is not possible, of course, with static passwords. The protocol can thus rely primarily on very fast symmetric-key commitment and decommitment rounds and explicit IMD testing of the condition α≈β, rather than minimal-knowledge cryptographic comparison. The pairing protocol has two phases: (1) a secure channel set-up phase, which involves lightweight use of public-key cryptography to create a secure but unauthenticated channel between the IMD 102-*i* and the monitoring device 104 and (2) an authentication phase, in which the two devices use a commitment/decommitment scheme to check whether α≈β.

In the secure channel set-up phase, the IMD 102-*i* and the monitoring device 104 establish a secure channel. In some embodiments, the secure channel may be established via transport layer security (TLS). The IMD 102-*i* assumes the role of the TLS client and the monitoring device 104 that of a TLS server. That is, only the monitoring device 104 presents a certificate. When instantiated with RSA, TLS requires little client computation, just one low-exponent (e-$2^{16}$+1) modular exponentiation.

The pairing protocol makes use of an output from the TLS session, referred to herein as a label s. Given that at least one of the two entities is honest, s is random and thus unique (with overwhelming probability). It isn't secret, however. In practice, s might be, e.g., the hash of the TLS session key. For convenience, the details of TLS are modeled simply as a protocol SecChannel in FIG. 7 which outputs random label s.

SecChannel creates a secure channel in the sense that it provides confidentiality, integrity, and freshness. But it doesn't provide authentication—the IMD 102-*i* doesn't present a certificate, and doesn't validate the certificate of the monitoring device 104. When an IMD 102-*i* first sets up a secure channel, it has no assurance that it has paired with a valid monitoring device 104, i.e., one actually in contact with the patient. Similarly, the monitoring device 104 doesn't know if it's communicating with a valid IMD. Thus, the secure channel set-up phase is followed by an authentication phase.

In the authentication phase, the two devices commit to their respective PV readings α and β. Each device binds its commitments to the label s of the secure channel on which it is communicating, preventing its re-use, prior to decommitment, on a different channel. The IMD 102-*i* can then safely decommit α for the monitoring device 104, as it has already received a commitment for β.

If the monitoring device 104 determines that α≈β, then it decommits β. Otherwise, it rejects the session. This selective decommitment helps ensure that the monitoring device 104 only reveals β to a valid IMD 102-*i* (one that knows α≈β), preventing re-use of β by an adversary. If the monitoring device 104 had been the party who decommits first, an adversary would have easily mounted a man-in-the-middle attack.

The IMD 102-*i* itself then verifies that α≈β, and makes an accept/reject authentication decision. After an invalid authentication attempt, IMD 102-*i* waits a full PV read cycle before accepting a new authentication request. This delay prevents interleaving attacks, in which a session with the monitoring device 104 overlaps with two IMD sessions.

Figure 7:
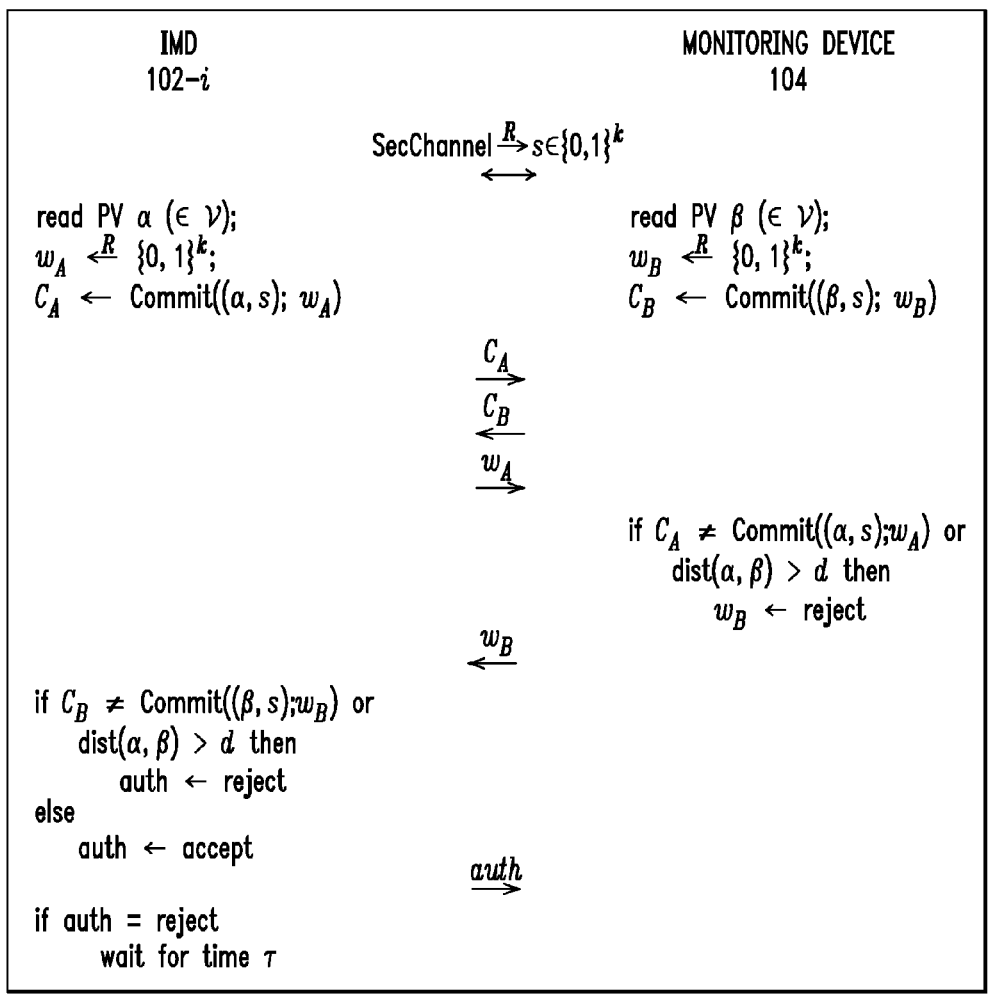
FIG. 7 illustrates an algorithm for performing a pairing protocol, according to an embodiment of the invention.

The authentication protocol is thus specified in FIG. 7. $\mathcal{V}$ is defined as the space of valid PVs. Let dist: $\mathcal{V} \times \mathcal{V} \rightarrow \mathbb{R}_0^+$ denote a pairwise distance metric on $\mathcal{V}$. Let τ denote the time required for a device to read a PV and let Commit denote a commitment scheme with message space $\mathcal{V}$ and key space $\{0,1\}^k \times \{0,1\}^k$. A commitment of message pair (m,s)∈$\mathcal{V}$×$\{0,1\}^k$ under key w∈$\{0,1\}^k$ is denoted by C=Commit((m,s); w). A convention of decommitment as verification of correct commitment is adopted, i.e., decommiting m under key w involves the check C= Commit((m,s); w) For simplicity, Commit is treated as an ideal functionality, i.e., as unconditionally hiding and binding. When either device outputs the message reject, rejecting the session, it terminates communication on the session channel. Additionally, devices support only serial sessions, not concurrent ones.

A security analysis of the pairing protocol is provided below. An adversary Adv is assumed that fully controls the channel between the IMD 102-$i$ and the monitoring device 104, i.e., Adv can deliver, drop, modify, and forge messages as desired. Adv, however, cannot corrupt the IMD 102-$i$ or the monitoring device 104. $\alpha$ and $\beta$ are assumed to be readings by the IMD 102-$i$ and monitoring device 104, respectively, which come from probability distributions defined by a model $\mathcal{M}$. Given $\mathcal{M}$, $p_1$ denotes the maximum probability that Adv can guess a valid PV reading in one try, i.e., given legitimate PV reading $\alpha$, that Adv can guess a $\nu$ such that dist($\nu,\alpha$)≤d. Similarly, $p_2$ denotes the maximum probability that Adv does so in exactly two tries. More precisely, given simultaneous PV readings $\alpha$ and $\beta$, $p_2$ is the maximum probability, given a known, failed guess for $\alpha$, that Adv guesses a valid PV reading correctly for $\beta$.

The security of an exemplary H2H system is defined in terms of an experiment in which Adv succeeds if it can authenticate to the IMD 102-$i$, i.e., cause it to output accept for a session with Adv on SecChannel To convey intuition for the resistance of H2H to man-in-the-middle attacks, we give the following description of an Adv attack. Here $\text{succ}_{Adv}^{H2H}$(1,1) denotes the probability that Adv succeeds when it initiates a single session each with the monitoring device 104 and the IMD 102-$i$. Thus, for PV model $\mathcal{M}$, $\text{succ}_{Adv}^{H2H}(1,1) \leq p_1 + p_2 - p_1 p_2$.

Adv's goal is to initiate a session on SecChannel with the IMD 102-$i$ such that it outputs accept. To do so, Adv must send the IMD 102-$i$ a simulated commitment for the monitoring device 104 $C_B'$, with a corresponding value $\beta'$ such that dist($\alpha, \beta'$)≤d. Commit is modeled as an indeal functionality, both unconditionally hiding and binding. As the commitment $C_A$ of the IMD 102-$i$ is thus hiding, Adv can obtain an advantage over random guessing for $\beta'$ only by interacting additionally with the monitoring device 104.

Suppose, therefore, that Adv has initiated a session with the monitoring device 104 prior to completion of its session with the IMD 102-$i$. Adv sends the monitoring device 104 a simulated commitment for the IMD 102-$i$ $C_A''$ on PV $\alpha''$. Thus the Adv-IMD 102-$i$ session has session label s' and the Adv-monitoring device 104 session has session label s" such that s"≠s'. For simplicity, the negligible probability event s"=s' is ignored.

Two cases arise, depending on whether Adv sends the simulated monitoring device commitment $C_B'$ to the IMD 102-$i$ before or after sending a decommitment $w_A''$ to the monitoring device 104.

If the commitment $C_B'$ precedes the decommitment $w_A''$, $C_B$ is bound to label s". To cause the IMD 102-$i$ to accept, however, $C_B'$ must be bound to label s'. Intuitively, binding commitments to SecChannel labels prevents Adv from "stitching together" two distinct channels in a man-in-the-middle attack. Given these bindings and the hiding property of Commit for $C_B$, then, Adv must commit to a PV $\beta'$ in $C_B'$ that is independent of PVs $\alpha$ and $\beta$. Thus Adv must guess $\beta'$ at random, and the IMD outputs accept with probability $p_1$.

If the commitment $C_B'$ follows decommitment $w_A''$, Adv sends $C_A''$ prior to any decommitments. As commitments are hiding, Adv commits in $C_A''$ to a PV $\alpha''$ that is independent of previous transcript values, and thus correct with probability at most $p_1$. On sending decommitment $w_A''$, Adv learns whether $\alpha''$ was correct. With this knowledge, Adv may then submit a PV guess $\beta'$ in $C_B'$ to the IMD 102-$i$ with success probability at most $p_2$. Thus, in this case Adv's maximum success probability is $p_1 + (1-p_1)p_2$.

Thus, given a PV model $\mathcal{M}$ and $q=q_i+q_r$ with even-valued q, $\text{succ}_{Adv}^{H2H}(q_i,q_r) \leq 1 - (p_1 + p_2 - p_1 p_2)^{q/2}$, reflecting that Adv's best strategy against H2H systems is to initiate sessions simultaneously with the IMD 102-$i$ and the monitoring device 104, which respectively read PVs $\alpha$ and $\beta$. Adv tries to authenticate to monitoring device 104 by guessing $\beta$. If this fails, Adv tries to authenticate to IMD 102-$i$ by guessing $\alpha$; it gains a small advantage from knowing that its guess for $\beta$ was incorrect.

For H2H systems, $\mathcal{M}_{H2H}$ and $\text{dist}_{H2H}$ denote the PV distribution model and Neyman-Pearson-induced distance metric respectively for an H2H system. As such, for given PV model $M_{H2H}$ and distance metric $\text{dist}_{H2H}$, and $q=q_i+q_r$ with even-valued q, $\text{succ}_{Adv}^{H2H}(q_i,q_r) \leq 1-(1-2p_1)^{q/2}$. In other words, the probability of a successful attack in a given session by Adv is at most twice its authentication probability.

A more detailed analysis of the security of H2H systems is provided below. The process of PV sampling can be modeled in terms of a set $\mathcal{V}$ of PV values and a pair of functions (sample, noise). The PV model for H2H systems $\mathcal{M} = (\mathcal{V}$; (sample, noise)). At the time of PV reading a true PV $\gamma$ is sampled from $\mathcal{V}$ under a distribution defined by probabilistic function sample(t,$\tau$)→$\gamma \in \mathcal{V}$, where t denotes the sampling time and $\tau$ denotes the sampling interval length. The sample (t,$\tau$) and sample (t+$\tau$,$\tau'$) are assumed to be i.d.d. for any $\tau' \geq \tau$. The sample (t,$\tau$) is also assumed to be identically distributed for any t, i.e., that it is a stationary processs. Thus we let sample (·,$\tau$) denote a PV sample of duration i taken at an arbitrary time.

Noise in the PV reading by the IMD 102-$i$ and the monitoring device 104 are modeled respectively by $\alpha \leftarrow$ noise($\gamma$) and $\beta \leftarrow$ noise($\gamma$), for probabilistic function noise: $\mathcal{V} \rightarrow \mathcal{V}$. The model can also be adjusted for different noise in the IMD 102-$i$ and the monitoring device 104.

The cryptographic model treats SecChannel as an ideal functionality. A player P can invoke SecChannel with any other player P' of its choice. The functionality then outputs a unique label s$\in\{0,1\}^k$ to P and P', or else outputs a failure symbol $\bot$. All messages labeled with s are privately delivered between P and P'; an adversary can block messages, but otherwise can't see, modify, or reorder them. Honest players support only one instance of SecChannel at a given time. Commit is also treated as an ideal functionality, i.e., perfectly hiding and binding. The adversary Adv can at any time cause the monitoring device 104 to initiate a session or itself initiate a session with IMD 102-$i$.

The adversarial model assumes a monitoring device 104 and an IMD 102-$i$ executing serial sessions uncorrupted by Adv. Security is defined with respect to an experiment involving an adversary Adv that knows $\mathcal{M}$ and fully controls the channel between the IMD 102-$i$ and the monitoring device 104. There is a query interface send that communicates messages to the IMD and Programmer. Adv may send arbitrary queries m of the form send(entity, m) for entity E (IMD 102-$i$, monitoring device 104). A special query send(entity, start) causes a device to initiate the H2H protocol, i.e., execute SecChannel. To cause the IMD 102-$i$ and the monitoring device 104 to pair, Adv calls send(monitoring device 104, start), then communicates message send(IMD 102-$i$, start) from the monitoring device 104 to IMD 102-$i$.

If the Adv sends at most $q_i$ start queries to the IMD 102-$i$ and $q_r$ start queries to the monitoring device 104 over the course of a security analysis, $\text{succ}_{Adv}^{H2H}(q_1, q_r)$ is the probability that Adv causes the IMD **102-*i*** to output accept for a session where it communicates with Adv on SecChannel To present the result, the probability $p_1$ that making an unconditioned query, i.e., knowing M only, Adv can successfully guess a valid PV, is defined as $$p_1 = \max_{a' \in \mathcal{V}}(pr[\text{dist}(a',a) \leq d | a \leftarrow \text{noise}(\gamma), \gamma \leftarrow \text{sample}(\bullet, \tau)]).$$

The probability $p_1$ may be thought of as a type of minentropy. The probability $p_2$ is defined as $$p_2 = \max_{a',b' \in \mathcal{V}}(pr[\text{dist}(a',a) \leq d | \text{dist}(b',b) > d, a \leftarrow \text{noise}(\gamma), b \leftarrow \text{noise}(\gamma), \gamma \leftarrow \text{sample}(\bullet, \tau)]).$$

The probability $p_2$ is the maximum probability, given a failed PV guess b' for β, that Adv can guess a valid PV a' for a.

The Adv maximizes its probability of success by making q/2 pairs of queries to the IMD **102-*i* and the monitoring device 104, and that its success probability for each pair of queries is at most $\text{succ}_{Adv}^{H2H}(1,1)$. The Adv maximizes its probability of success by making q/2 pairs of queries to the IMD 102-*i* and the monitoring device 104**. Adv's success probability for each pair of queries is at most $\text{succ}_{Adv}^{H2H}(1,1)$.

Given output reject, the IMD **102-*i* waits a full cycle (time t) before initiating another session (taking input start). If the IMD 102-*i* initiates local session i at time t, and thus reads $\alpha_t \leftarrow \text{noise}(\text{sample}(t,\tau))$, then the IMD 102-*i* will only initiate a fresh session i+1 at time $\geq t+\tau$. Again, the i used to represent the local sessions is distinct from the i used to represent the bit position and in IMD 102-*i*. Thus, if the monitoring device 104 initiates a session with PV β, then β will be independent of $\alpha_i$ provided that β is read at time t+τ or later. Since the monitoring device 104 only initiates a session at time t+τ, any monitoring device 104 PV reading β is independent of at least one of $\alpha_i$ and $\alpha_{i+1}$. In general, then, any PV reading by the monitoring device 104** correlates with at most one $\alpha_i$.

Consequently, Adv can make at most one conditioned query, i.e., query with information about γ, per unconditioned query. It can do so only by initiating overlapping sessions with the IMD **102-*i* and the monitoring device 104**. Given q queries in total, Adv can create at most q/2 such sessions.

Thus, $\text{succ}_{Adv_{q_1,q_r}}^{H2H} \leq 1 - (1 - \text{succ}_{Adv}^{H2H})^{q/2}$. H2H systems have two distinct properties of uniformity which simplify the analysis. First, the PV probability model $\mathcal{M}_{H2H}$ has PVs which are distributed uniformly at random (but correlated). That is, $\alpha, \beta \in_U \mathcal{V}$. The Neyman-Pearson-derived distance metric $\text{dist}_{H2H}$ also has uniform regions of validity, that is the number of valid PV guesses β is identical for any α in $\mathcal{V}$. The distance between two PVs depends on their bit differences, not the PVs' specific bit values.

This can be shown be letting $R_\alpha = \{v | \text{dist}(v, \alpha) \leq d\}$ and $R_\beta = \{v | \text{dist}(v, \beta) \leq d\}$, with $|R_\alpha| = |R_\beta| = r$. If Adv has failed, with probability $p_1$, to guess α correctly, i.e., guessed a value $v_1 \notin |R_\alpha|$ then given the uniformly random PVs in H2H systems, the Adv's best strategy for guessing β is to select a value $v_2$ uniformly at random from $\mathcal{V} - R_\alpha$. This is true given some further assumptions that β is an unbiased estimator of α. Thus, $p_2 = pr[v_2 \in R_\beta] < r/(|\mathcal{V}| - r) = p_1(1 - p_1)$, as $p_1 = r/|\mathcal{V}|$.

H2H systems protect patient privacy in two senses. First, the IMD **102-*i* doesn't release a public key (a monitoring device 104** does), or any other static identifier. As a is random, and protocol values are random (or pseudorandom), H2H systems thus provide logical-layer tracking privacy; an adversary can't correlate distinct RF sightings of a given IMD, i.e., can't track a patient wirelessly from a distance. Second, the randomness of a prevents leakage of medically significant data, e.g., cardiac abnormalities that might be detectable in a full ECG waveform.

An IMD **102-*i* in some embodiments may consist of three boards: (1) an ultra low-power microcontroller, such as TI MSP430F5438; (2) an ECD analog A/D front end, such as TI ADS1298; and (3) a wireless sensor modem, such as TI CC430F5137. The MSP430 is a 16-bit TI micro-controller with a single address space for instructions and data. It has one of the lowest reported power-consumption profiles in the industry. As such, it is attractive for embedded processing applications such as IMDs. In this implementation, microcontroller communications with the ECG analog front end and the wireless board are based on the RS-232 and SPI standards, respectively. Both serial interfaces are implemented in the MSP430. The MSP430 also extracts ECG features and communicates with the monitoring device 104** using TLS.

The IMD **102-*i* and the monitoring device 104 can establish a channel between them using TLS. The IMD 102-*i* performs the operations of an ordinary TLS client and the monitoring device 104 those of an ordinary server. TLS is designed to provide an encrypted and authenticated channel between two communicating parties. Standard TLS authentication assumes a PKI, however, which H2H systems do not. Thus the one deviation from normal TLS usage in H2H systems is that the IMD 102-*i* does not verify the monitoring device 104**'s certificate against a PKI. Instead, H2H touch-to-access authentication, i.e., ECG PV comparison, is performed after the TLS handshake to authenticate the channel Some embodiments use RSA for the master secret key exchange in TLS, AES-128 for encryption, and SHA256 as the hash function. SHA256 also serves as the commitment function Commit(.) in the pairing protocol. RSA is chosen for key exchange because RSA encryption with a small public exponent is the fastest key-exchange option for TLS. The RSA public exponent may be set to $2^{16}+1$. The RSA modulus and message length are set to 2048 bits to conform to current NIST key length recommendations. It is important to note, however, that embodiments are not limited solely to the protocols and values above.

Some embodiments of H2H require a cryptographically secure pseudo-random number generator (PRNG) for RSA ciphertext padding, key generation and nonce selection in TLS, and commitment. Embodiments mat use a NIST-recommended PRNG based on cipher-block chaining (CBC), with AES as the underlying block cipher. The PRNG requires an initial random seed, which may be generated offline and stored in a non-volatile memory of the IMD. In a commercial IMD, it can be set at the time of manufacture.

To annotate ECG R-peaks, some embodiments of H2H apply a simple length transformation to the ECG waveform using an open-source algorithm called "WQRS." In this algorithm, the arc length of the waveform over a moving window is compared against a threshold to detect heartbeats. An implementation of WQRS is available on the PhysioNet website, which is incorporated by reference herein.

In the TLS standard, the client, i.e., IMD **102-*i*, initiates communication. Under Federal Communications Commission (FCC) regulations, however, the IMD 102-*i* should wait for a request from the monitoring device 104 before communicating, so as to preserve the IMD 102-*i***'s limited energy. One possible way to operate the IMDs under this requirement is to put the MSP430 in sleep mode, with periodic wake-up intervals in which it polls the receiving channel. This periodic wake-up approach is not power-efficient, though, because of the frequent unnecessary transitions between sleep and wake modes. The MSP430 has a feature that enables it to hibernate while its peripherals are still running Using this feature, embodiments can implement an additional, low-power and low-bandwidth paging radio channel that wakes up the MSP430 and causes it to initiate communication.

H2H systems may also be used in conjunction with various other authentication systems. For example, a distance bounding technique which involves implantation of a piezo device in the patient may be used. The device may generate a random key and emit it acoustically such that a monitoring device 104 can only receive the key at close range to the living organism. Such an approach, however, is generally limited to implantation at a depth of 1 cm or less from the skin, which would rule out incorporation into a deep-body IMD or would require a separate implanted device. Another distance bounding technique involves ultrasound-based authentication of a monitoring device 104 to an IMD 102-$i$. The ultrasound-based technique, however, requires RF shielding which adds to the complexity of an IMD.

As another example, shielding techniques may be used in conjunction with H2H systems. Shielding techniques use a device known as a shield which is worn near the body and used to authenticate/mediate communication with an IMD. The shield may comprise a full duplex radio device acting as a jammer-cum-receiver, which simultaneously listens to and jams IMD messages as appropriate. Similarly, a device may be worn external to the body which authenticates on behalf of an IMD. H2H can be incorporated with such techniques so as to provide security when a patient does not have access to or chooses not to wear the shield or other external device.

These and numerous other alternative embodiments within the scope of the appended claims will be readily apparent to those skilled in the art.

What is claimed is:

1. A method performed by a medical device, comprising:
    storing information used to derive a first probability distribution of obtaining a physiological value without physical contact with the living organism yielding designated errors and information used to derive a second probability distribution of a valid monitoring device obtaining the physiological value yielding the designated errors;
    receiving from a monitoring device a request for access to the medical device configured for implantation into a living organism from a monitoring device;
    measuring a physiological value of the living organism;
    performing a pairing protocol with the monitoring device, the pairing protocol comprising a secure channel set-up phase followed by an authentication phase; and
    permitting access by the monitoring device responsive to a successful pairing in accordance with the pairing protocol, the successful pairing being based at least in part on a determination that a physiological value supplied by the monitoring device substantially matches the measured physiological value;
    wherein the medical device performs the secure channel set-up phase before sending the measured physiological value to the monitoring device;
    wherein the measured physiological value sent to the monitoring device comprises a committed value, the committed value being bound to information determined based at least in part on the secure channel set-up phase;
    wherein the supplied physiological value and the measured physiological value each comprise two or more portions;
    wherein the determination that the supplied physiological value substantially matches the measured physiological value is based at least in part on:
        determining differences between corresponding ones of the two or more portions of the respective physiological values; and
        comparing said differences to an error threshold; and
    wherein the error threshold comprises different error rates for respective ones of the two or more portions.

2. A non-transitory processor-readable storage medium having instruction code embodied therein which when executed by a processor implements the steps of the method of claim 1.

3. A method performed by a monitoring device, comprising:
    sending a request for access to a medical device configured for implantation into a living organism;
    supplying a physiological value to the medical device;
    performing a pairing protocol with the medical device, the pairing protocol comprising a secure channel set-up phase followed by an authentication phase; and
    obtaining access to the medical device responsive to a successful pairing in accordance with the pairing protocol, the successful pairing being based at least in part on a determination that the supplied physiological value substantially matches a physiological value measured by the medical device;
    wherein the monitoring device performs the secure channel set-up phase before supplying the physiological value to the medical device;
    wherein the physiological value supplied to the monitoring device comprises a committed value, the committed value being bound to information determined based at least in part on the secure channel set-up phase;
    wherein the supplied physiological value and the measured physiological value each comprise two or more portions;
    wherein the determination that the supplied physiological value substantially matches the measured physiological value is based at least in part on:
        determining differences between corresponding ones of the two or more portions of the respective physiological values; and
        comparing said differences to an error threshold; and
    wherein the error threshold comprises different error rates for respective ones of the two or more portions.

4. A non-transitory processor-readable storage medium having instruction code embodied therein which when executed by a processor implements the steps of the method of claim 3.

5. An apparatus comprising:
    a medical device configured for implantation into a living organism, the medical device comprising processing circuitry, a memory, and interface circuitry configured for communication with a monitoring device, the medical device being configured to:
        receive a request for access from the monitoring device;
        measure a physiological value of the living organism;
        perform a pairing protocol with the monitoring device, the pairing protocol comprising a secure channel set-up phase followed by an authentication phase; and
        permit access by the monitoring device responsive to a successful pairing in accordance with the pairing protocol, the successful pairing being based at least in part on a determination that a physiological value supplied by the monitoring device substantially matches the measured physiological value;
    wherein the medical device performs the secure channel set-up phase before sending the measured physiological value to the monitoring device;

wherein the medical device is further configured to:
store information used to derive a first probability distribution of obtaining a physiological value without physical contact with the living organism yielding designated errors; and
store information used to derive a second probability distribution of a valid monitoring device obtaining the physiological value yielding the designated errors;
wherein the determination that the supplied physiological value substantially matches the measured physiological value is based at least in part on an analysis of the supplied physiological value, the first probability distribution and the second probability distribution; and
wherein the second probability distribution is modeled using a binomial distribution based on a pre-computed statistical error rate for each bit position in the measured physiological value, wherein two or more bit positions in the measured physiological value have different error rates.

6. An apparatus comprising:
a medical device configured for implantation into a living organism, the medical device comprising processing circuitry, a memory, and interface circuitry configured for communication with a monitoring device, the medical device being configured to:
receive a request for access from the monitoring device;
measure a physiological value of the living organism;
perform a pairing protocol with the monitoring device, the pairing protocol comprising a secure channel set-up phase followed by an authentication phase; and
permit access by the monitoring device responsive to a successful pairing in accordance with the pairing protocol, the successful pairing being based at least in part on a determination that a physiological value supplied by the monitoring device substantially matches the measured physiological value;
wherein the medical device performs the secure channel set-up phase before sending the measured physiological value to the monitoring device;
wherein the measured physiological value sent to the monitoring device comprises a committed value, the committed value being bound to information determined based at least in part on the secure channel set-up phase;
wherein the supplied physiological value and the measured physiological value each comprise two or more portions;
wherein the determination that the supplied physiological value substantially matches the measured physiological value is based at least in part on:
determining differences between corresponding ones of the two or more portions of the respective physiological values; and
comparing said differences to an error threshold; and
wherein the error threshold comprises different error rates for respective ones of the two or more portions.

7. The apparatus of claim 6, wherein the measured physiological value is based at least in part a plurality of time-sensitive random values taken over a given time interval.

8. The apparatus of claim 7, wherein the plurality of time-sensitive random values are derived from electrocardiography measurements taken over the given time interval.

9. The apparatus of claim 8, wherein an inter-pulse interval of the living organism has a set of physiologically significant features, the plurality of time-sensitive random values being derived from sets of physiologically significant features for one or more inter-pulse intervals in the given time interval.

10. The apparatus of claim 6, wherein the medical device is further configured to:
store information used to derive a first probability distribution of obtaining a physiological value without physical contact with the living organism yielding designated errors; and
store information used to derive a second probability distribution of a valid monitoring device obtaining the physiological value yielding the designated errors;
wherein the determination that the supplied physiological value substantially matches the measured physiological value is based at least in part on an analysis of the supplied physiological value, the first probability distribution and the second probability distribution.

11. The apparatus of claim 10, wherein the medical device is further configured to:
compute an error value of the supplied physiological value, the error value being based at least in part on a total number of mismatches between corresponding bits in the supplied physiological value and the measured physiological value; and
determine whether the supplied physiological value substantially matches the measured physiological value based at least in part on the results of a Neyman-Pearson hypothesis test using the error value, the first probability distribution and the second probability distribution.

12. The apparatus of claim 11, wherein the medical device determines that the supplied physiological value substantially matches the measured physiological value when $$\log\left(\frac{P(u)}{Q(u)}\right) > Th$$

wherein u is the error value, P(u) is a probability of obtaining the measured physiological value without contact with the living organism yielding error value u, Q(u) is a probability of a valid monitoring device obtaining the measured physiological value yielding error value u, and Th is a fixed threshold value.

13. The apparatus of claim 12, wherein the fixed threshold value Th is pre-computed based on a target false negative rate.

14. The apparatus of claim 10, wherein the first probability distribution is modeled using a binomial distribution having a designated Bernoulli trial probability.

15. The apparatus of claim 6, wherein the information determined based at least in part on the secure channel set-up phase comprises an output of the secure channel set-up phase.

16. The apparatus of claim 6, wherein the secure channel set-up phase is based at least in part on public-key cryptography and comprises establishing a secure channel via transport layer security (TLS), wherein the medical device acts as a TLS client and the monitoring device acts as a TLS server.

17. The apparatus of claim 6, wherein the authentication phase comprises:
committing, in the medical device, to the measured physiological value to determine the committed value;
binding, in the medical device, the committed value to a label of a secure channel determined in the secure channel set-up phase to determine a first bound value;
sending, from the medical device to the monitoring device, the first bound value;
receiving, in the medical device, a second bound value from the monitoring device;
decommitting, in the medical device, the first bound value to determine a first decommittment value;

sending, from the medical device to the monitoring device, the first decommittment value;

receiving, in the medical device, a second decommittment value;

determining the supplied physiological value using the second bound value and the second decommittment value; and granting the request for access if the supplied physiological value substantially matches the measured physiological value.

18. The apparatus of claim 6, wherein the successful pairing comprises a transient pairing.

19. The apparatus of claim 6, wherein the measured physiological value is valid for a given time interval, and wherein when a first instance of the pairing protocol in the given time interval is unsuccessful, subsequent requests for access during the given time interval are rejected.

20. The apparatus of claim 6, wherein the measured physiological value comprises a first number of independent and identically distributed random bits, and wherein the supplied physiological value substantially matches the measured physiological value when a second number of bits in the supplied physiological value are equal to corresponding bits in the measured physiological value.

21. The apparatus of claim 6, wherein the medical device is further configured to permit access to the medical device by the monitoring device when respective bits of the measured physiological value corresponds to bits in one or more identified patterns, at least one of the one or more identified patterns corresponding to a life-threatening medical event in the living organism.

22. The apparatus of claim 6, wherein the medical device comprises an implantable cardioverter defibrillator.

23. The apparatus of claim 6, wherein access to the medical device permits the monitoring device to read data corresponding to the living organism from the memory of the medical device.

24. The apparatus of claim 6, wherein access to the medical device permits the monitoring device to reprogram the medical device.

25. An apparatus comprising:

a monitoring device comprising processing circuitry and interface circuitry configured for communication with one or more medical devices configured for implantation into a living organism, the monitoring device being configured to:

send a request for access to a given one of the medical devices;

supply a physiological value to the given medical device;

perform a pairing protocol with the given medical device the pairing protocol comprising a secure channel set-up phase followed by an authentication phase; and obtain access to the given medical device responsive to a successful pairing in accordance with the pairing protocol, the successful pairing being based at least in part on a determination that the supplied physiological value substantially matches a physiological value of the living organism measured by the given medical device;

wherein the monitoring device performs the secure channel set-up phase before supplying the physiological value to the medical device;

wherein the physiological value supplied to the monitoring device comprises a committed value, the committed value being bound to information determined based at least in part on the secure channel set-up phase;

wherein the supplied physiological value and the measured physiological value each comprise two or more portions;

wherein the determination that the supplied physiological value substantially matches the measured physiological value is based at least in part on:

determining differences between corresponding ones of the two or more portions of the respective physiological values; and comparing said differences to an error threshold; and wherein the error threshold comprises different error rates for respective ones of the two or more portions.

\* \* \* \* \*

UNITED STATES PATENT AND TRADEMARK OFFICE
CERTIFICATE OF CORRECTION

PATENT NO. : 8,886,316 B1
APPLICATION NO. : 13/718171
DATED : November 11, 2014
INVENTOR(S) : Ari Juels Page 1 of 1

It is certified that error appears in the above-identified patent and that said Letters Patent is hereby corrected as shown below:

In the specification:

Column 8, line 53, after "from" please change "a" to -- $\alpha$ --

Column 11, line 40, after "value" please change "a" to -- $\alpha$ --

Column 11, line 52, after "whether" please change "$\alpha \approx \alpha$" to -- $\alpha \approx \beta$ --

Column 14, line 59, after "for entity" please change "E" to -- $\in$ --

Column 14, line 66, after "most" please change "q," to -- $q_i$ --

Column 15, line 1, please change "($q_l$,$q_r$)" to --($q_i$,$q_r$) --

Column 15, line 5, after "knowing" please change "M" to -- $\mathcal{M}$ --

Column 15, line 43, please change $$succ^{H2H}_{Adv_{q_l,q_r}} \leq 1-(1-succ_{Adv}{}^{H2H})^{q/2}$$

to $$succ^{H2H}_{Adv_{q_l,q_r}} \leq 1 - (1 - succ^{H2H}_{Adv_{1,1}})^{q/2}$$

In the claims:

Claim 1, column 17, line 38, before "living organism" please change "the" to -- a --

Claim 1, column 17, line 43, after "implantation into" please change "a" into -- the --

Signed and Sealed this
Seventeenth Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,886,316 B1
APPLICATION NO. : 13/718171
DATED : November 11, 2014
INVENTOR(S) : Ari Juels, Masoud Rostami and Farinaz Koushanfar Page 1 of 1

It is certified that error appears in the above-identified patent and that said Letters Patent is hereby corrected as shown below:

TITLE PAGE: ITEM 72

In the section labeled "Inventor", after "Ari Juels, Brookline, MA (US)" please add --Masoud Rostami, Houston, TX (US); Farinaz Koushanfar, Houston, TX (US)--

Signed and Sealed this
Thirty-first Day of March, 2015

Michelle K. Lee
*Director of the United States Patent and Trademark Office*